(12) United States Patent
Lee

(10) Patent No.: US 10,994,122 B2
(45) Date of Patent: May 4, 2021

(54) ELECTRICAL STIMULATION DEVICE

(71) Applicant: Y-BRAIN INC., Daejeon (KR)

(72) Inventor: Kiwon Lee, Daejeon (KR)

(73) Assignee: Y-BRAIN INC., Daejeon (KR)

( * ) Notice: Subject to any disclaimer, the term of this patent is extended or adjusted under 35 U.S.C. 154(b) by 0 days.

(21) Appl. No.: 15/492,923

(22) Filed: Apr. 20, 2017

(65) Prior Publication Data

US 2017/0216593 A1 Aug. 3, 2017

Related U.S. Application Data

(63) Continuation of application No. PCT/KR2015/010607, filed on Oct. 7, 2015.

(30) Foreign Application Priority Data

Oct. 22, 2014 (KR) .................. 10-2014-0143228

(51) Int. Cl.
*A61N 1/04* (2006.01)
*A61N 1/36* (2006.01)

(52) U.S. Cl.
CPC ......... *A61N 1/0456* (2013.01); *A61N 1/0476* (2013.01); *A61N 1/0492* (2013.01); *A61N 1/36034* (2017.08); *A61N 1/36025* (2013.01)

(58) Field of Classification Search
None
See application file for complete search history.

(56) References Cited

U.S. PATENT DOCUMENTS

| | | | | |
|---|---|---|---|---|
| 2004/0167461 A1* | 8/2004 | Nitzan | ........... | A61N 1/044 604/20 |
| 2008/0288026 A1* | 11/2008 | Cross | ........... | H01R 13/5224 607/60 |
| 2009/0171418 A1* | 7/2009 | Sarif | ........... | A61H 39/002 607/59 |
| 2010/0030129 A1* | 2/2010 | Nitzan | ........... | A61N 1/044 604/20 |
| 2014/0206974 A1* | 7/2014 | Volpe | ........... | A61N 1/3975 600/388 |
| 2014/0222105 A1* | 8/2014 | Broderick | ........... | A61N 1/0412 607/59 |

FOREIGN PATENT DOCUMENTS

| | | |
|---|---|---|
| JP | 2013544175 A | 12/2013 |
| KR | 1019870004713 A | 6/1987 |
| KR | 1019880007099 A | 8/1988 |
| KR | 1019880010791 A | 10/1988 |
| KR | 1020000064573 A | 11/2000 |

OTHER PUBLICATIONS

International Search Report for PCT/KR2015/010607 dated Jan. 14, 2016.

\* cited by examiner

*Primary Examiner* — Ankit D Tejani
(74) *Attorney, Agent, or Firm* — Studebaker & Brackett PC

(57) ABSTRACT

An electrical stimulation device is provided. According to one embodiment of the present invention, the electrical stimulation device for applying an electrical stimulation to the skin of a user comprises: a patch layer, which is a single patch layer and makes contact with the skin of the user when the electrical stimulation device is worn by or attached to the user; and a plurality of patch segments formed to be spaced apart from each other on the patch layer and transmitting current to the patch layer.

10 Claims, 8 Drawing Sheets

ELECTRICAL STIMULATION DEVICE

CROSS-REFERENCE TO RELATED APPLICATIONS

The present application is a continuation of International Patent Application No. filed PCT/KR2015/010607 filed Oct. 7, 2015, which is based upon and claims the benefit of priority to Korea Patent Application No. 10-2014-0143228 filed on Oct. 22, 2014.

The disclosures of the above-listed applications are hereby incorporated by reference herein in their entirety.

BACKGROUND

Embodiments of the inventive concept described herein relate to an electrical stimulation device, and more particularly, relate to an electrical stimulation device for monitoring voltage or current supplied to a user if electrical stimulation is provided to the user using the electrical stimulation device.

It has been known that technology for brain electrical stimulation using transcranial direct current stimulation (tDCS) is effective to increase cognitive abilities and treat mental diseases such as depression and attention deficit hyperactivity disorder (ADHD).

Therefore, if the technology for brain electrical stimulation is used in everyday life, brain functions may be improved. Mental disorders may be cured by continuously stimulating or suppressing connections between nerves.

However, a conventional electrical stimulation device may only stimulate a head of a user based on voltage or current set for brain stimulation. It may fail to be prepared for a case where electrical stimulation progresses using voltage or current which is higher than set voltage or current since a problem is encountered in the electrical stimulation device. Therefore, if the user uses the conventional electrical stimulation device, there are fears that burns will occur on skin of the user due to unexpected high voltage or current.

SUMMARY

Embodiments of the inventive concepts provide an electrical stimulation device for dividing a patch layer into a plurality of areas to control the plurality of areas.

Embodiments of the inventive concept provide an electrical stimulation device for preventing a burn from occurring on skin of a user due to high voltage or high current using a monitoring unit which may monitor voltage or current supplied to each of a plurality of patch segments.

Embodiments of the inventive concept provide an electrical stimulation device for minutely verifying a region to which high voltage or high current is supplied by measuring voltage or current supplied to a plurality of segments formed to be spaced apart from each other on a patch layer which is in contact with skin of a user.

The technical problems to be solved by the present inventive concept are not limited to the aforementioned problems, and any other technical problems not mentioned herein will be clearly understood from the following description by those skilled in the art to which the present disclosure pertains.

According to an aspect of an embodiment, an electrical stimulation device for providing electrical stimulation to skin of a user may include a patch layer configured to be a single patch layer and be in contact with the skin of the user if the electrical stimulation device is worn or attached to the user and a plurality of patch segments configured to be formed to be spaced apart from each other on the patch layer and transmit current to the patch layer.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Hereinafter, a description will be given in detail of exemplary embodiments of the inventive concept with reference to the accompanying drawings. Advantages, features, and methods of accomplishing the same will become apparent with reference to embodiments described in detail below together with the accompanying drawings. However, the inventive concept is not limited by embodiments disclosed hereinafter, and may be implemented in various forms. Rather, these embodiments are provided to so that this disclosure will be through and complete and will fully convey the concept of the invention to those skilled in the art, and the inventive concept will only be defined by the appended claims. Like reference denotations refer to like elements throughout the specification.

Unless otherwise defined herein, all terms (including technical and scientific terms) used in the specification may have the same meaning that is generally understood by a person skilled in the art. Also, terms which are defined in a dictionary and commonly used should be interpreted as not in an idealized or overly formal detect unless expressly so defined.

Terms used in the specification are used to describe embodiments of the inventive concept and are not intended to limit the scope of the inventive concept. In the specification, the terms of a singular form may include plural forms unless otherwise specified. The expressions "comprise" and/or "comprising" used herein indicate existence of one or more other elements other than stated elements but do not exclude presence of additional elements.

Hereinafter, a description will be given of an electrical stimulation device according to embodiments of the inventive concept with reference to drawings.

Figure 1:
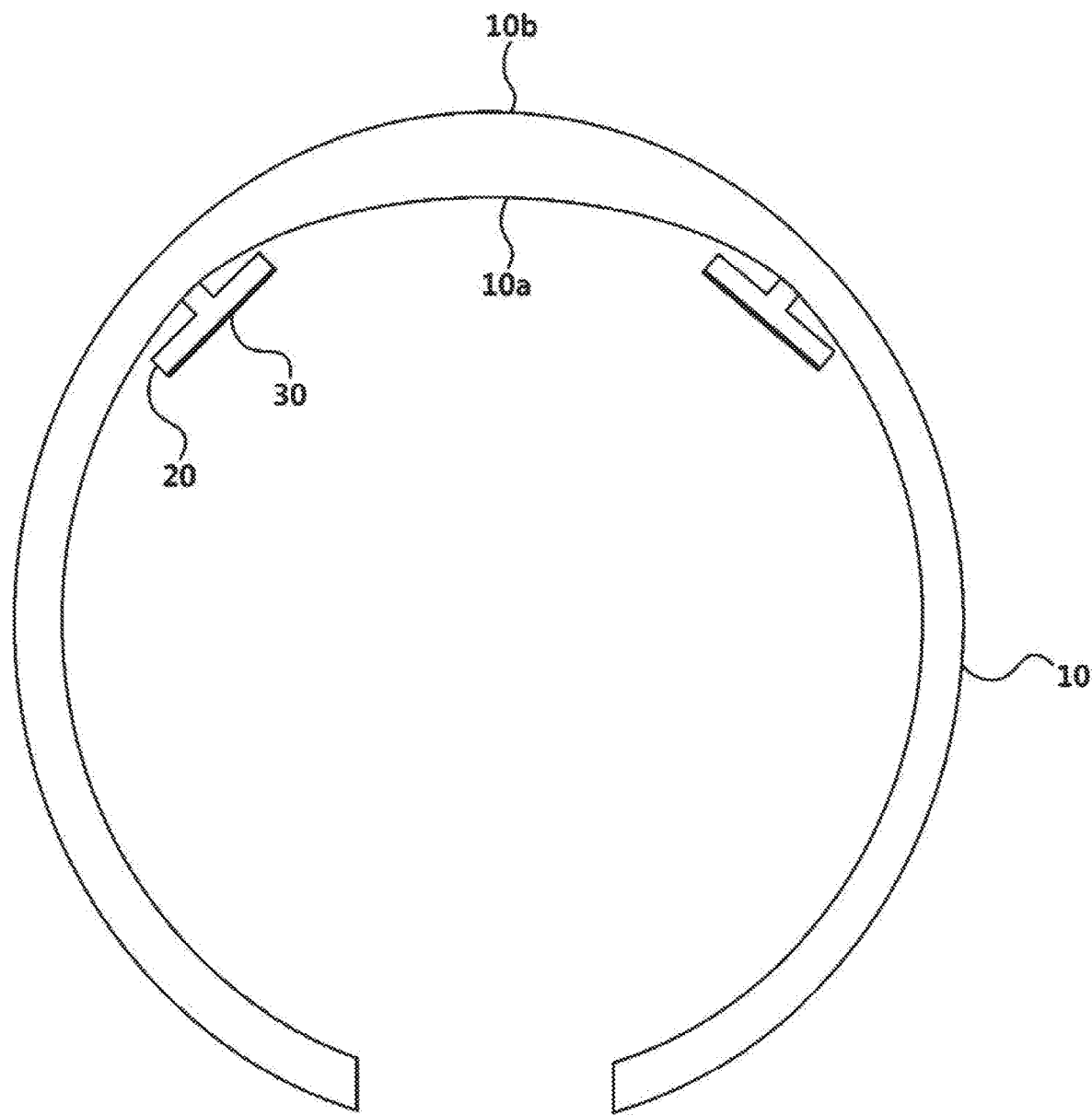
FIG. 1 is a drawing illustrating a schematic configuration of an electrical stimulation device according to an embodiment of the inventive concept.
Figure 2:
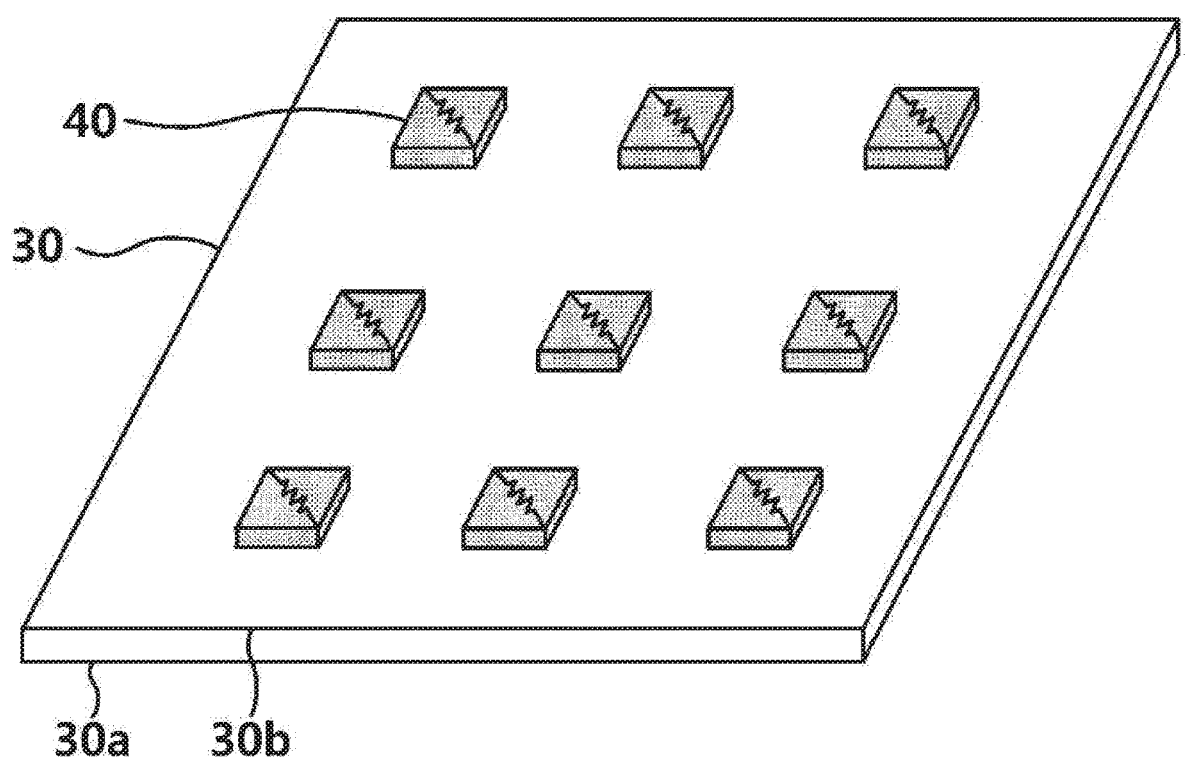
FIG. 2 is a drawing illustrating a patch layer and a plurality of patch segments included in FIG. 1.

Referring to FIGS. 1 and 2, a description will be given of an electrical stimulation device according to an embodiment of the inventive concept. Referring to FIG. 1, a schematic configuration of the electrical stimulation device according to an embodiment of the inventive concept is illustrated. Referring to FIG. 2, a patch layer 30 and a plurality of patch segments 40 included in FIG. 2 are illustrated.

First of all, referring to FIG. 1, the electrical stimulation device according to an embodiment may include a frame 10, an electrode part 20 attached to the frame 10, and the patch layer 30 which is in contact with skin of a user if he or she wears or attaches the electrical stimulation device. In detail, the electrode part 20 may be attached to an inner surface 10a of the frame 10 having the inner surface 10a and an outer surface 10b, and the patch layer 30 may be attached to one end of the electrode part 20. If the user wears or attaches the electrical stimulation device to his or her head, the patch layer 30 may be in contact with his or her head. In the specification, an embodiment is exemplified as the electrical stimulation device which stimulates the head of the user. However, technique features of the inventive concept may be applied to an electrical stimulation device which simulates another body portion of the user except for the head. Further, the entire shape of the electrical stimulation device is not limited to FIG. 1.

Although not illustrated in FIG. 1, referring to FIG. 2, the plurality of patch segments 40 may be formed on the patch layer 30. In detail, the patch layer 30 may include a first surface 30a which is in contact with skin of the user if he or she wears or attaches the electrical stimulation device and a second surface 30b opposite to the first surface 30a. The plurality of patch segments 40 may be formed on the second surface 30b of the patch layer 30.

The patch layer 30 may be a single thing, particularly, may be formed as a single layer. The patch layer 30 may include, for example, hydrogel and may be formed of high-resistivity material. Thus, since the patch layer 30 has high impedance, a current density of an edge portion of the patch layer 30 may be prevented from being increased due to an edge-effect. Therefore, a constant current density may be maintained in the entire region of the patch layer 30, thus stably providing electrical stimulation using the electrical stimulation device according to an embodiment of the inventive concept.

In general, skip may contain dead skin cells having relatively high impedance and elements except for the dead skin cells, having relatively low impedance. Since current easily flows along the elements except for the dead skin cells, having the relatively low impedance, current may be concentrated on a constant region to flow.

However, according to the electrical stimulation device according to an embodiment of the inventive concept, the patch layer 30 may be formed of high-resistivity material and may have high impedance. Thus, an influence by an impedance difference between if current flows to dead skin cells via the patch layer 30 and if current flows to the elements except for the dead skin cells via the patch layer 30 may be reduced. Thus, current may be prevented from being concentrated on part of skin to flow, and a current density is evenly established in the entire region of skin which is in contact with the patch layer 30. Thus, according to the electrical stimulation device according to an embodiment of the inventive concept, electrical stimulation may be stably provided via the patch layer 30.

Meanwhile, resistivity of material forming the patch layer 30 may be higher than that of material forming the plurality of patch segments 40. However, embodiments of the inventive concept are not limited thereto.

The patch layer 30 may include a chloride ion. Since the chloride ion is included in skin of the user, the skin of the user and the patch layer 30 which is in contact with the skin of the user may include a common ion. Therefore, since overpotential formed between the electrode part 20 and the skin of the user is reduced, stimulation of an unnecessary level may be prevented from being provided to the skin of the user. Thus, according to the electrical stimulation device according to an embodiment of the inventive concept, electrical stimulation may be stably provided via the patch layer 30.

Referring to FIG. 2, the plurality of patch segments 40 may be formed to be spaced apart from each other on the patch layer 30. There may be no limit to a shape of each of the plurality of patch segments 40 or an interval between the plurality of patch segments 40. Since each of the plurality of patch segments 40 is electrically connected with the patch layer 30, it may transmit current to the patch layer 30. As described above, the plurality of patch segments 40 may be formed of low-resistivity material, thus efficiently transmitting current to the patch layer 30.

The plurality of patch segments 40 may fail to be elements which are in direct contact with skin of the user and may provide electrical stimulation to the user via the patch layer 30 by being formed on the single patch layer 30 and transmitting current to the patch layer 30. Herein, since the plurality of patch segments 40 are formed on the patch layer 30, each of the plurality of patch segments 40 may be controlled to obtain an effect of dividing the patch layer 30 into a plurality of portions to control the plurality of portions.

Figure 3:
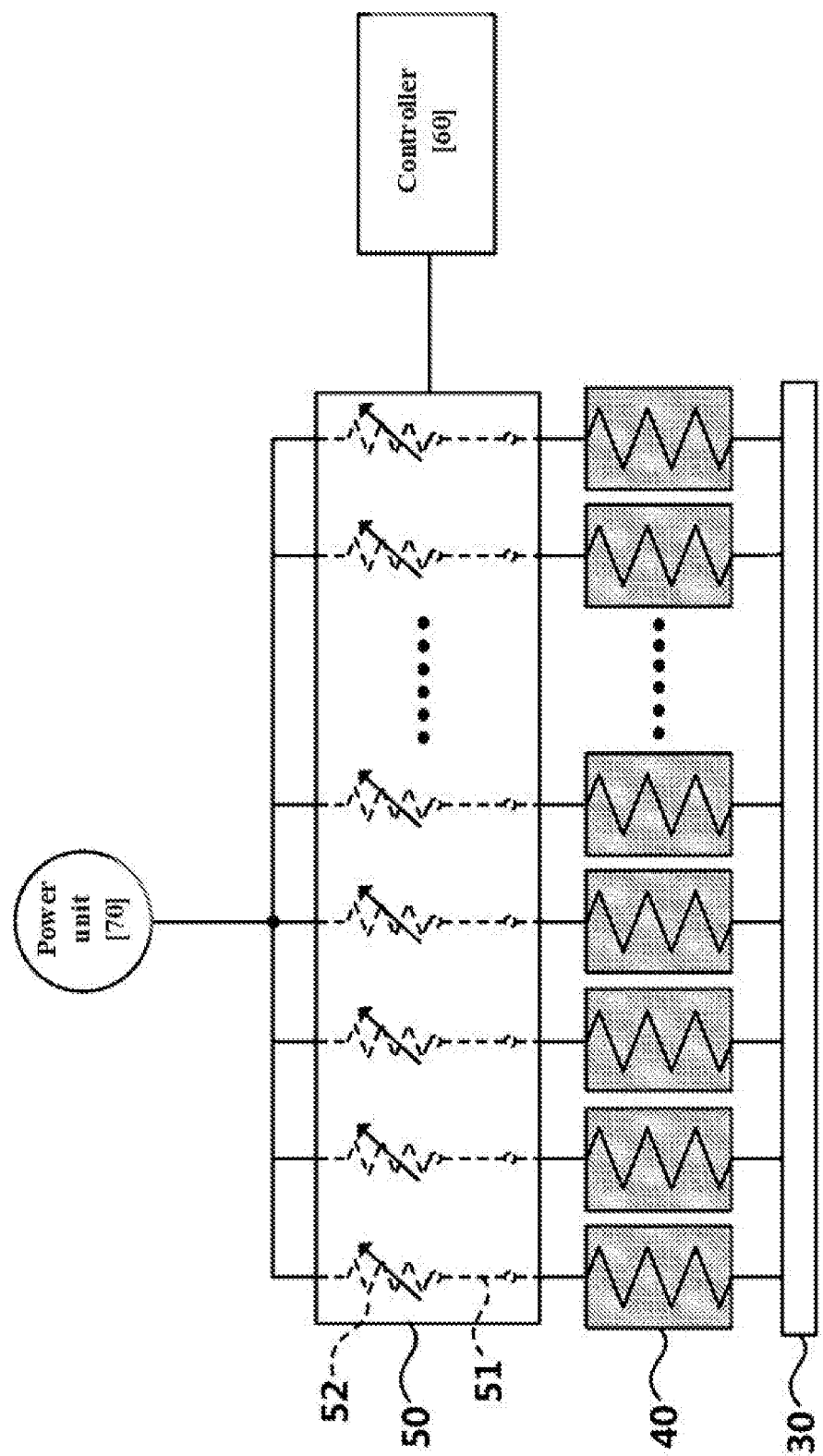
FIGS. 3 and 4 are drawings illustrating a schematic configuration of an electrical stimulation device according to another embodiment of the inventive concept.
Figure 4:
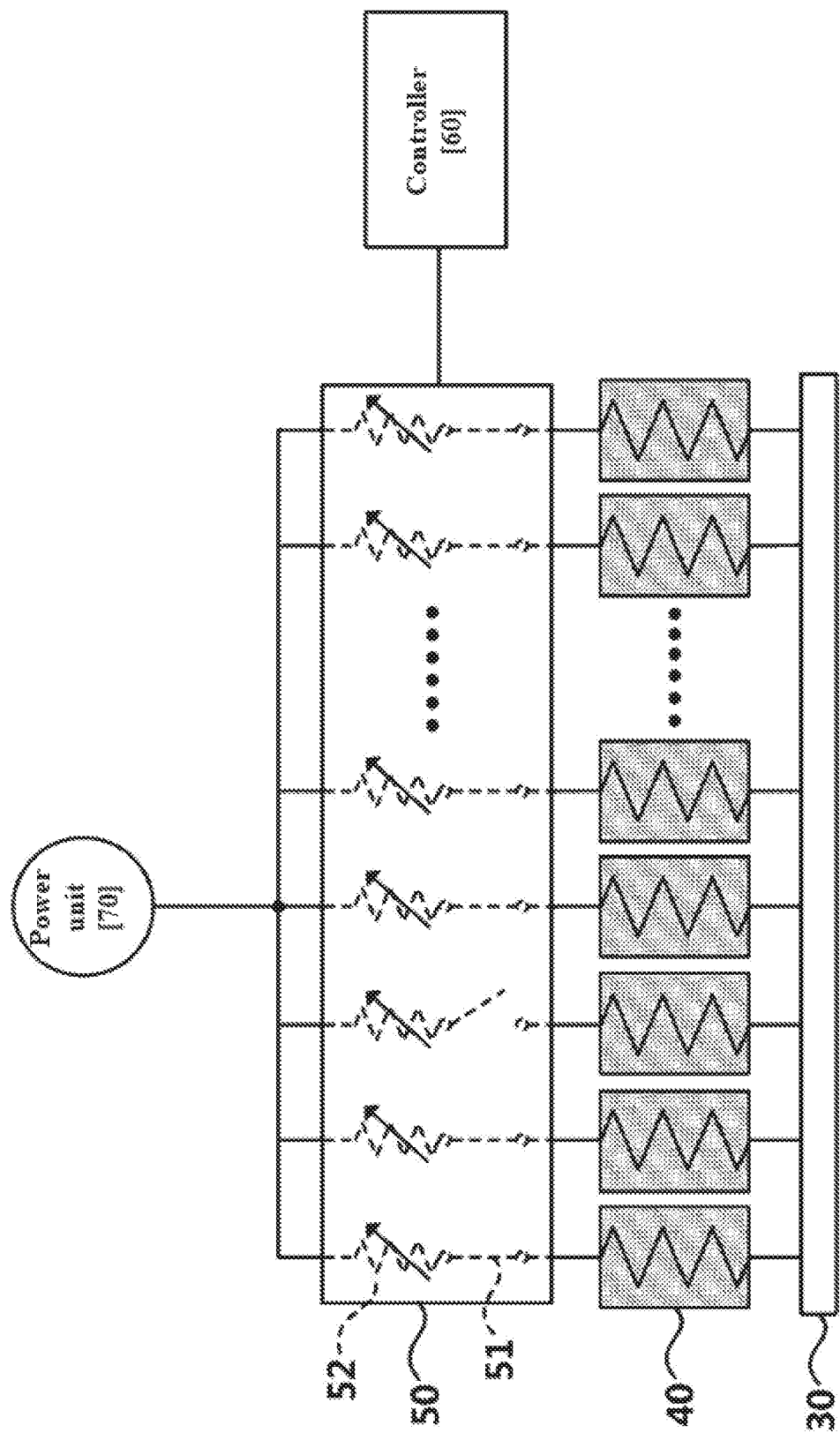

Hereinafter, referring to FIGS. 3 and 4, a description will be given of an electrical stimulation device according to another embodiment of the inventive concept. Herein, a description will be given of a difference with an electrical stimulation device according to an embodiment of the inventive concept shown in FIG. 2. Referring to FIGS. 3 and 4, a schematic configuration of the electrical stimulation device according to another embodiment of the inventive concept is illustrated.

Referring to FIG. 3, the electrical stimulation device according to another embodiment of the inventive concept may further include a blocking and adjustment unit 50 for blocking or adjusting voltage or current supplied to each of a plurality of patch segments 40 and a controller 60 for controlling an operation of the blocking and adjustment unit 50.

The blocking and adjustment unit 50 may block or adjust voltage or current supplied to the specific patch segment 40 among the plurality of patch segments 40 based on control of the controller 60. If necessary, the blocking and adjustment unit 50 may block or adjust voltage or current supplied to all of the plurality of patch segments 40. Thus, the plurality of patch segments 40 may be separately controlled by the blocking and adjustment unit 50.

In FIG. 3, an embodiment of the inventive concept is exemplified as the blocking and adjustment unit 50 is located between the power unit 70 and the plurality of patch segments 40. However, embodiments of the inventive concept are not limited thereto. For example, the blocking and adjustment unit 50 may be located between the plurality of patch segments 40 and the patch layer 30.

The blocking and adjustment unit 50 may include an element for blocking voltage or current, for example, a switch 51 and an element for adjusting voltage or current, for example, a variable resistor 52. Herein, the element for blocking voltage or current is not limited to the switch 51, and the element for adjusting voltage or current is not limited to the variable resistor 52. In FIG. 3, an embodiment of the inventive concept is exemplified as the blocking and adjustment unit 50 includes both of the switch 51 and the variable resistor 52. However, embodiments of the inventive concept are not limited thereto. For example, the blocking and adjustment unit 50 may include any one of the switch 51 and the variable resistor 52.

Referring to FIG. 4, the switch 51 may block voltage or current supplied to the patch segment 40 by being opened. The variable resistor 52 may adjust voltage or current supplied to the patch segment 40 by being changed in resistance level.

The plurality of patch segment 40 may transmit current to the patch layer 30. If voltage or current supplied to the specific patch segment 40 is blocked, a region of the patch layer 30, which is in contact with the specific patch segment 40, may fail to no longer receive current from the specific patch segment 40. Further, if voltage or current supplied to the specific patch segment 40 is adjusted to be reduced, an amount of current transmitted from the specific patch segment 40 may be reduced in the region of the patch layer 30, which is in contact with the specific patch segment 40.

Therefore, the electrical stimulation device according to another embodiment of the inventive concept may control an amount of current transmitted to a region of the patch layer 30, which is in contact with each of the plurality of patch segments 40 by adjusting voltage or current supplied to each of the plurality of patch segments 40 using the blocking and adjustment unit 50. In other words, the patch layer 30 may be divided into a plurality of regions to be controlled.

Figure 5:
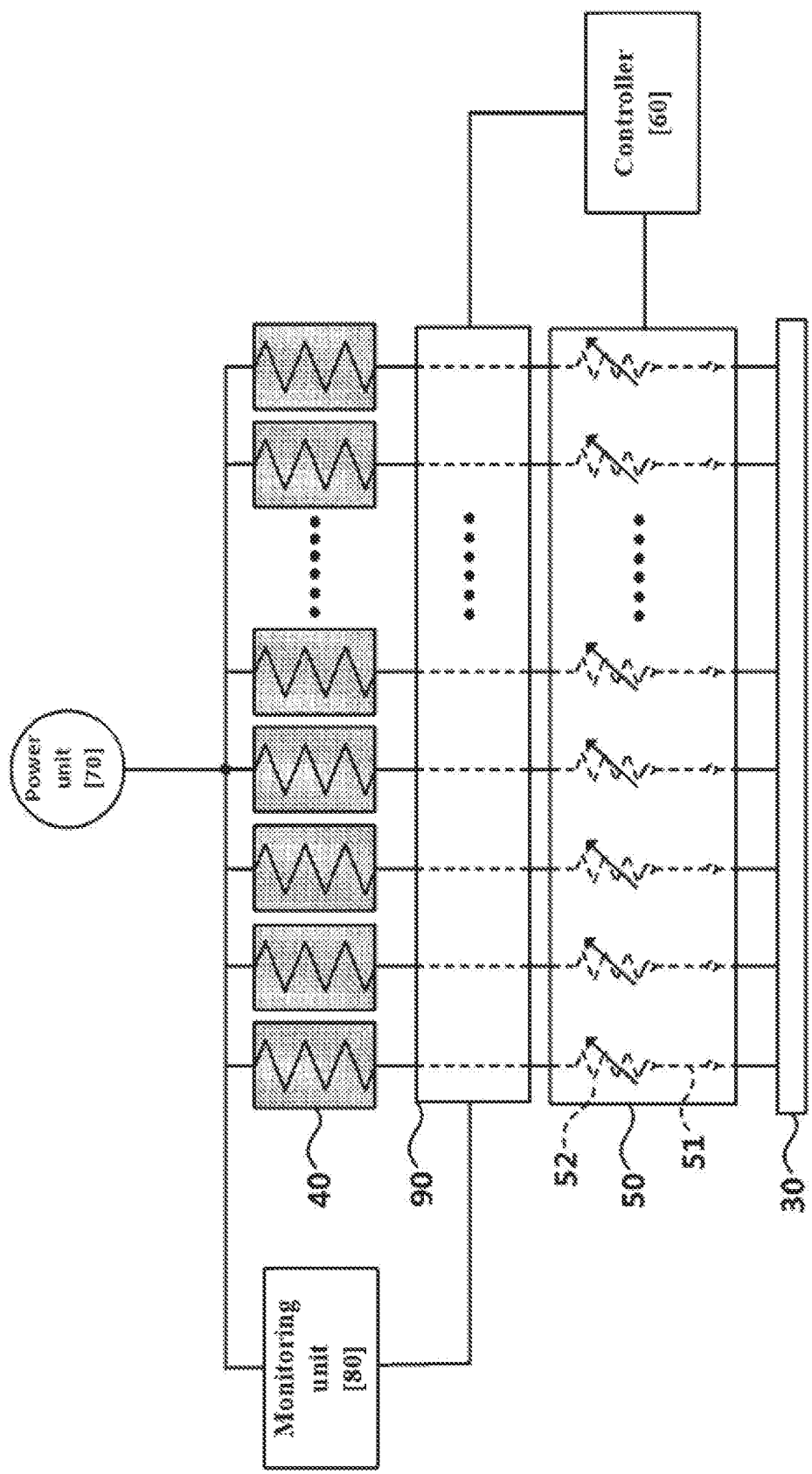
FIG. 5 is a drawing illustrating a schematic configuration of an electrical stimulation device according to another embodiment of the inventive concept.

Hereinafter, referring to FIG. 5, a description will be given of an electrical stimulation device according to another embodiment of the inventive concept. Herein, a description will be given of a difference with an electrical stimulation device according to another embodiment of the inventive concept shown in FIG. 3. Referring to FIG. 5, a schematic configuration of the electrical stimulation device according to another embodiment of the inventive concept is illustrated.

[Voltage Monitoring]

Referring to FIG. 5, the electrical stimulation device according to another embodiment of the inventive concept may further include a monitoring unit 80 for measuring voltage or current supplied to each of the plurality of patch segments 40 and a connection selecting unit 90 for connecting the patch segment 40 to be measured to the monitoring unit 80. Herein, in FIG. 5, the monitoring unit 80 may be shown as an element which may measure voltage supplied to the plurality of patch segments 40.

Meanwhile, in some embodiments, the electrical stimulation device may be implemented except a blocking and adjustment unit 50. For convenience of description, in FIG. 5, an embodiment of the inventive concept is exemplified as the blocking and adjustment unit 50 is located between a plurality of patch segments 40 and a patch layer 50 contrary to FIG. 4. However, embodiments of the inventive concept are not limited thereto. For example, the blocking and adjustment unit 50 may be located between the plurality of patch segments 40 and the power unit 70.

Meanwhile, the connection selecting unit 90 may be located between, for example, the plurality of patch segments 40 and the patch layer 30. An operation of the connection selecting unit 90 may be controlled by a controller 60. As a state where each of the plurality of patch segments 40 is connected with the patch layer 30 is maintained, the patch segment 40 to be measured among the plurality of patch segments 40 may be connected with the monitoring unit 80 by the connection selecting unit 90. For example, the connection selecting unit 90 may have, but is not limited to, a configuration of a multiplexer.

To measure voltage supplied to each of the plurality of patch segments 40, one end of the monitoring unit 80 may be connected to the connection selecting unit 90, and the other end of the monitoring unit 80 may be connected with an upper end of the plurality of patch segments 40. Since the connection selecting unit 90 is connected with a lower end of the plurality of patch segments 40, the monitoring unit 80 may measure voltage supplied to the plurality of patch segments 40 by connecting to upper and lower ends of the plurality of patch segments 40.

Herein, for the monitoring unit 80 to monitor all voltages supplied to the plurality of patch segments, the connection selecting unit 90 may continuously change the plurality of patch segments 40 connected with the monitoring unit 80. For example, the controller 60 may control the connection selecting unit 90 such that each of the plurality of patch segments 40 measures voltage at a constant interval.

If the monitoring unit 80 verifies that high voltage or high current is supplied to the plurality of patch segments 40, the controller 60 may block voltage or current supplied to the plurality of patch segments for safety of a user. In this regard, a description will be given of various embodiments. Herein, the scope and spirit of the inventive concept is not limited by the exemplified embodiments.

First, if voltage or current measured by the monitoring unit 80 is greater than or equal to a predetermined voltage or current, the controller 60 may control the blocking and adjustment unit 50 to block voltage or current supplied to each of the plurality of patch segments 40. In other words, if the voltage or current measured by the monitoring unit 80 is greater than or equal to the predetermined voltage or current, since high voltage or high current is supplied to the plurality of patch segments and the patch layer 30, there may be fears that a burn will occur on skin of the user, which is in contact with the patch layer 30. Thus, the user may be protected by stopping electrical stimulation by the electrical stimulation device such that voltage or current is not supplied to the plurality of patch segments 40. Thus, according to the electrical stimulation device according to another embodiment of the inventive concept, the user may stably use the electrical stimulation device without concern for burns.

Second, if the voltage or current measured by the monitoring unit 80 is greater than or equal to the predetermined voltage or current, the controller 60 may control the blocking and adjustment unit 50 to block or adjust voltage or current supplied to the patch segment 40 measured as the supplied voltage or current is greater than or equal to the predetermined voltage or current. In other words, although high voltage or high current is supplied to some patch segments 40, the controller 60 may block or adjust voltage or current supplied to some patch segments 40 in which a problem is encountered without blocking voltage or current supplied to all of the plurality of patch segments 40. Therefore, efficiency may be increased in operating the electrical stimulation device according to another embodiment of the inventive concept.

Third, if voltage or current supplied to the specific patch segment 40, measured by the monitoring unit 80, is greater than voltage or current supplied to the other patch segment 40, measured by the monitoring unit 80, by a predetermined rate or more, the controller 60 may prevent voltage or current from being supplied to the plurality of patch segments 40 or may block or adjust voltage or current supplied to the patch segment 40 to which relatively high voltage or current is supplied.

In detail, if the plurality of patch segments 40 includes first and second patch segments, if voltage or current measured as being supplied to the first patch segment by the monitoring unit 80 is greater than voltage or current measured as being supplied to the second patch segment by the monitoring unit 80 by a predetermined rate or more, the controller 60 may control the blocking and adjustment unit 50 to block voltage or current supplied to each of the plurality of patch segments 40 or block or adjust voltage or current supplied to the first patch segment to which relatively high voltage or current is supplied.

Lastly, if current which flows in the specific patch segment 40, measured by the monitoring unit 80, is greater than an average of voltages or currents supplied to the other patch segments 40, measured by the monitoring unit 80, by a predetermined rate or more, the controller 60 may control the blocking and adjustment unit 50 to block voltage or current supplied to each of the plurality of patch segments or block or adjust voltage or current supplied to the specific patch segment 40 to which relatively high voltage or current is supplied.

Figure 6:
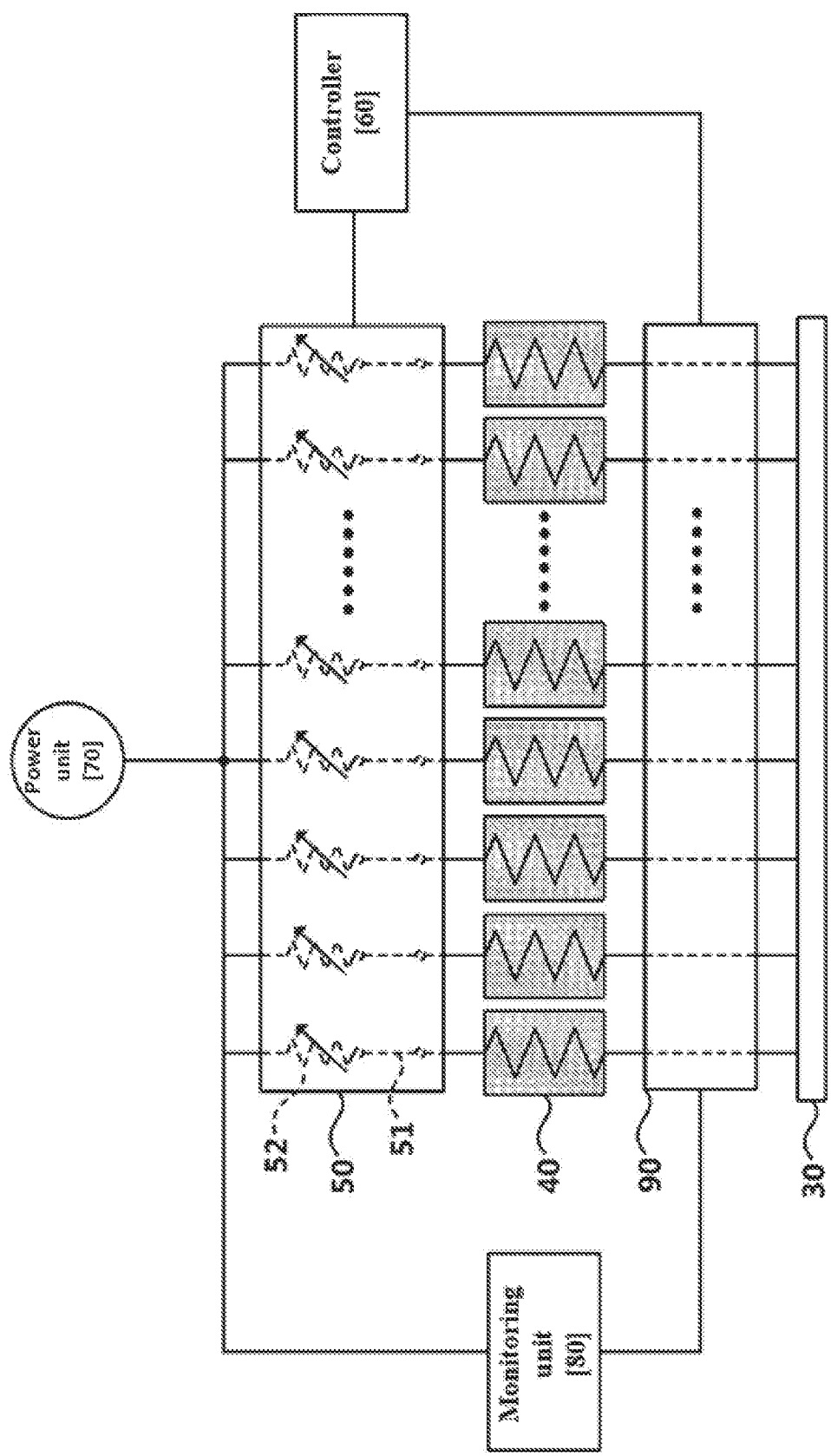
FIG. 6 is a drawing illustrating a schematic configuration of an electrical stimulation device according to another embodiment of the inventive concept.

Hereinafter, referring to FIG. 6, a description will be given of an electrical stimulation device according to another embodiment of the inventive concept. Herein, a description will be given of a difference with an electrical stimulation device according to another embodiment of the inventive concept shown in FIG. 5. Referring to FIG. 6, a schematic configuration of the electrical stimulation device according to another embodiment of the inventive concept is illustrated.

Referring to FIG. 6, the electrical stimulation device according to another embodiment of the inventive concept may have a difference with the electrical stimulation device according to another embodiment of the inventive concept shown in FIG. 5 in that a blocking and adjustment unit 50 is located between a power unit 70 and a plurality of patch segments 40.

In detail, to measure voltage supplied to the plurality of patch segments 40, one end of a monitoring unit 80 may be connected to a connection selecting unit 90, and the other end of the monitoring unit 80 may be connected to the power unit 70. Since the power unit 70 is connected with an upper end of the plurality of patch segments 40, the monitoring unit 80 may measure voltage supplied to the plurality of patch segments 40 by being connected with both of upper and lower ends of the plurality of patch segments 40. In some embodiments, the monitoring unit 80 may measure voltage supplied to the plurality of patch segments 40 by setting a level of a variable resistor 52 to "0".

Figure 7:
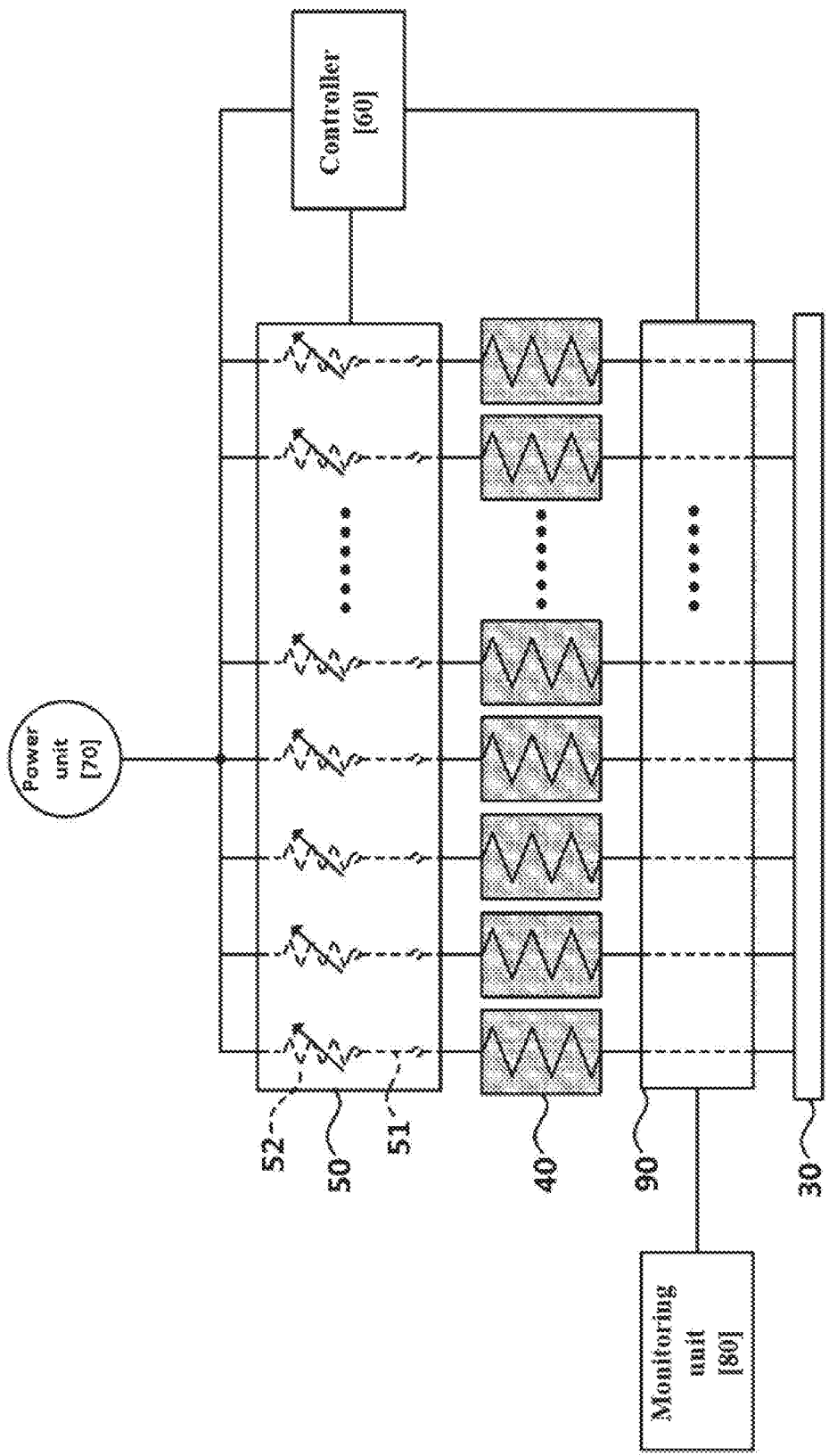
FIG. 7 is a drawing illustrating a schematic configuration of an electrical stimulation device according to another embodiment of the inventive concept.

Hereinafter, referring to FIG. 7, a description will be given of an electrical stimulation device according to another embodiment of the inventive concept. Herein, a description will be given of a difference with an electrical stimulation device according to another embodiment of the inventive concept shown in FIG. 5. Referring to FIG. 7, a schematic configuration of the electrical stimulation device according to another embodiment of the inventive concept is illustrated.

[Current Monitoring]

Referring to FIG. 7, elements which may allow a monitoring unit 80 to measure current supplied to the plurality of segments 40 are illustrated.

In detail, as a state where each of the plurality of patch segments 40 is connected with the patch layer 30 is maintained, the patch segment 40 to be measured among the plurality of patch segments 40 may be connected with the monitoring unit 80 by a connection selecting unit 90. Thus, the monitoring unit 80 may measure current supplied to each of the plurality of patch segments 40.

If the monitoring unit 80 verifies that high voltage or high current is supplied to the plurality of patch segments 40, a controller 60 may block voltage or current supplied to the plurality of patch segments 40 for safety of a user. In this regard, various embodiments described in the above-mentioned voltage monitoring may be applied to the current monitoring.

Figure 8A:
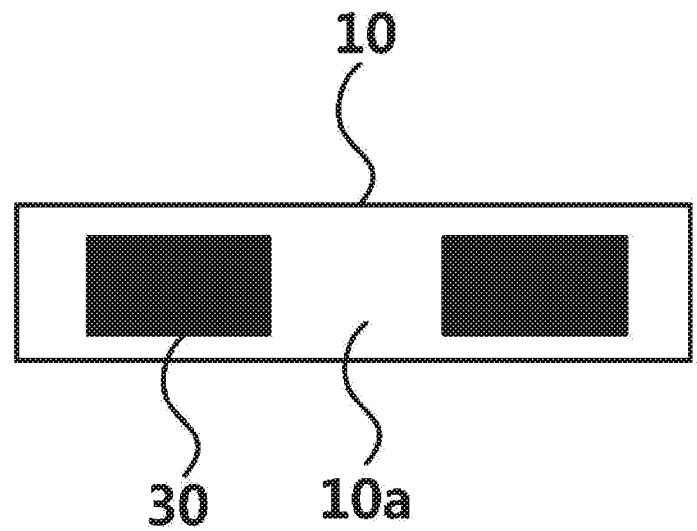
FIGS. 8A and 8B are drawings illustrating schematic configurations of electrical stimulation devices according to another embodiment of the inventive concept.
Figure 8B:
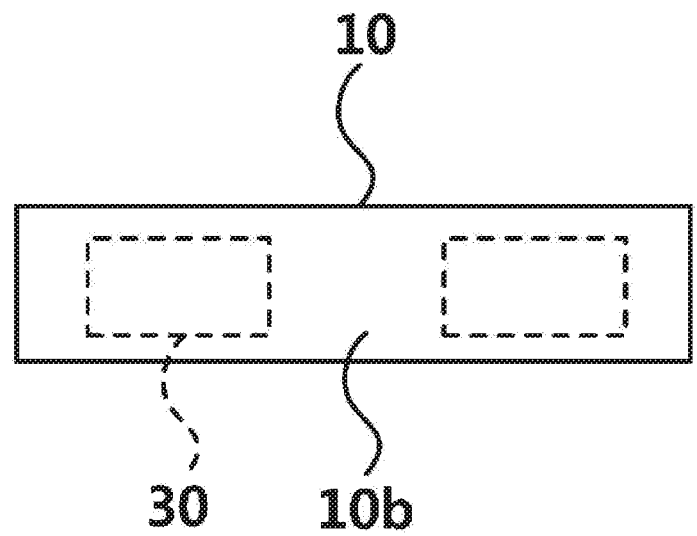

Hereinafter, referring to FIGS. 8A and 8B, descriptions will be given of electrical stimulation devices according to another embodiment of the inventive concept. Herein, a description will be given of a difference with an electrical stimulation device according to an embodiment of the inventive concept shown in FIG. 1. Referring to FIGS. 8A and 8B, schematic configurations of the electrical stimulation devices according to another embodiment of the inventive concept are illustrated.

Referring to FIGS. 8A and 8B, the electrical stimulation device according to another embodiment of the inventive concept may include a frame 10 and a patch layer 30 which is in contact with skin of a user if the electrical stimulation device is attached to him or her. Herein, contrary to the electrical stimulation device shown in FIG. 1, in the electrical stimulation device according to another embodiment of the inventive concept, the frame 10 may be of a band type.

In detail, an electrode part 20 may be attached to an inner surface 10a of the frame 10 having the inner surface 10a and an outer surface 10b, and the patch layer 30 may be attached to one end of the electrode part 20. If the user attaches the electrical stimulation device to his or her head, the patch layer 30 may be in contact with his or her head. Herein, in the specification, an embodiment of the inventive concept is exemplified as the electrical stimulation device which stimulates the head of the user. However, technical features of the inventive concept may be applied to an electrical stimulation device which stimulates another body portion of the user except for the head.

According to an embodiment of the inventive concept, an electrical stimulation device may prevent a burn from occurring on skin of a user due to high voltage or high current by including a monitoring unit which may monitor voltage or current supplied to a patch segment.

Further, the user may stably use the electrical stimulation device by stopping an operation of the electrical stimulation device if high voltage or high current is monitored by the monitoring unit.

Further, the electrical stimulation device may divide a patch layer into a plurality of areas to control the plurality of areas as a plurality of patch segments are formed on the patch layer.

While the inventive concept has been described with reference to embodiments, it will be apparent to those skilled in the art that various changes and modifications may be made without departing from the spirit and scope of the inventive concept. Therefore, it should be understood that the above embodiments are not limiting, but illustrative.

What is claimed is:

1. An electrical stimulation device for providing electrical stimulation to skin of a user, the device comprising:

a patch layer that is a single patch layer, the patch layer is configured to be in direct contact with the skin of the user when the electrical stimulation device is worn by or attached to the user;

a plurality of patch segments disposed on the patch layer and spaced apart from each other, the plurality of patch segments is configured to be in indirect contact with the skin of the user via the patch layer when the electrical stimulation device is worn by or attached to the user, and transmit current or voltage to the patch layer; and a blocking and adjustment unit configured to block or adjust voltage or current supplied to each of the plurality of patch segments, wherein the blocking and adjustment unit is directly connected with each of the plurality of patch segments, and wherein the patch layer includes hydrogel containing chloride ions, and the patch layer is further configured to receive the current or voltage, which is transmitted from the plurality of patch segments, and perform, by using the chloride ions contained in the hydrogel included in the patch layer, a direct application of the received current or voltage into a portion of the skin of the user, which is directly contacted with the patch layer, wherein the blocking and adjustment unit comprises a plurality of switches and a plurality of variable resistors, and wherein a respective switch of the plurality of switches is serially connected with a respective variable resistor of the plurality of variable resistors, and a respective combination of the respective switch and the respective variable resistor is configured to block voltage or current supplied to a respective patch segment of the plurality of patch segments.

2. The device of claim 1, further comprising:
a monitoring unit configured to measure voltage or current supplied to each of the plurality of patch segments.

3. The device of claim 2, further comprising:
a controller configured to control an operation of the blocking and adjustment unit,
wherein the controller is configured to:
when voltage or current measured by the monitoring unit is greater than or equal to a predetermined value of voltage or current, control the blocking and adjustment unit to block voltage or current supplied to each of the plurality of patch segments.

4. The device of claim 2, further comprising:
a controller configured to control an operation of the blocking and adjustment unit,
wherein the controller is configured to:
when voltage or current measured by the monitoring unit is greater than or equal to a predetermined value of voltage or current, control the blocking and adjustment unit to block or adjust voltage or current supplied to the patch segment measured as the supplied voltage or current is greater than or equal to the voltage or current.

5. The device of claim 2, further comprising:
a controller configured to control an operation of the blocking and adjustment unit,
wherein the plurality of patch segments comprises first and second patch segments,
wherein the monitoring unit is configured to measure a first voltage or current as being supplied to the first patch segment, and a second voltage or current as being supplied to the second patch segment, and
wherein the controller is configured to:
when a ratio of the measured first voltage or current to the measured second voltage or current is greater than a predetermined value, control the blocking and adjustment unit to block voltage or current supplied to each of the plurality of patch segments.

6. The device of claim 2, further comprising:
a controller configured to control an operation of the blocking and adjustment unit,
wherein the plurality of patch segments comprises first and second patch segments,
wherein the monitoring unit is configured to measure a first voltage or current as being supplied to the first patch segment, and a second voltage or current as being supplied to the second patch segment, and
wherein the controller is configured to:
when a ratio of the measured first voltage or current to the measured second voltage or current is greater than a predetermined value, control the blocking and adjustment unit to block or adjust voltage or current supplied to the first patch segment.

7. The device of claim 2, further comprising:
a controller configured to control an operation of the blocking and adjustment unit,
wherein the plurality of patch segments comprises first and second patch segments,
wherein the monitoring unit is configured to measure a first voltage or current as being supplied to the first patch segment and a second voltage or current as being supplied to the second patch segment,
wherein the controller is configured to, when a ratio of the measured first voltage or current to the measured second voltage or current is greater than a predetermined value, control the blocking and adjustment unit to block or adjust voltage or current supplied to the first patch segment, and
wherein the patch layer includes a region that is in contact with the first patch segment, the region is
configured to no longer transmit voltage or current from the first patch segment to the skin when the voltage or current supplied to the first patch segment is blocked, and
configured to transmit an adjusted amount of voltage or current from the first patch segment to the skin when the voltage or current supplied to the first patch segment is adjusted.

8. The device of claim 2, further comprising:
a connection selecting unit disposed on between the plurality of patch segments and the blocking and adjustment unit, and configured to selectively connect at least one patch segment corresponding to a measurement target among the plurality of patch segments to the monitoring unit.

9. The device of claim 1, wherein the patch layer has resistivity of material forming the patch layer, the resistivity being higher than resistivity of material forming the plurality of patch segments.

10. The device of claim 1, wherein the patch layer comprises a material having a resistivity configured to render an impedance of the patch layer to prevent a current density of an edge portion of the patch layer from increasing due to an edge-effect.

* * * * *